United States Patent [19]

Inde et al.

[11] Patent Number: 5,030,838
[45] Date of Patent: Jul. 9, 1991

[54] QUALITY INSPECTION DEVICE FOR PRINTED MATTER AND METHOD THEREOF

[75] Inventors: Akihiro Inde; Hiromitsu Ebihara, both of Toride, Japan

[73] Assignee: Komori Corporation, Tokyo, Japan

[21] Appl. No.: 462,701

[22] Filed: Jan. 9, 1990

[30] Foreign Application Priority Data

Jan. 12, 1989 [JP] Japan .................................. 1-3716

[51] Int. Cl.⁵ .......................................... G01N 21/86
[52] U.S. Cl. ................................... 250/559; 356/443
[58] Field of Search ............... 250/562, 563, 571, 572, 250/237 R, 559; 356/429, 430, 431, 443, 444

[56] References Cited

U.S. PATENT DOCUMENTS

| | | | |
|---|---|---|---|
| 3,413,065 | 11/1968 | Funk | 356/443 |
| 4,194,838 | 3/1980 | Bey et al. | 356/443 |
| 4,522,497 | 6/1985 | Ikin | 250/571 |

*Primary Examiner*—David C. Nelms
*Attorney, Agent, or Firm*—Abelman Frayne Rezac & Schwab

[57] ABSTRACT

Light received by a light receiving element in a quality inspection device for printed matter, is controlled to a constant value by passing the received light through a graduated neutral density filter that is adjusted in position relative to the optical axis of the light receiving element in dependence on the feed speed of the printed matter.

6 Claims, 5 Drawing Sheets

Camera density control circuit diagram

Processing flow

Camera density control circuit diagram

QUALITY INSPECTION DEVICE FOR PRINTED MATTER AND METHOD THEREOF

FIELD OF THE INVENTION

This invention relates to a quality inspection device for a printed matter and a method thereof, which specifically corrects changes in amounts of received light caused by changes in the feed speed of the printed matter.

BACKGROUND OF THE INVENTION

As a prior art quality inspection device for a printed matter, there has been proposed, for example, one which is shown in FIG. 7.

This is an example of this device applied to a sheet-feed printing machine having a plate cylinder 1 around which a printing plate is wound, a blanket cylinder 2 around which a rubber blanket is wound, and an impression cylinder 3 to apply a pressure, wherein an image is transferred from the printing plate to the rubber blanket and then printed on printing paper.

This device mainly comprises a camera unit 4 as a detector to take in the surface condition as image data of the printed paper fed to the impression cylinder 3, a lighting unit 5 to illuminate the printed paper surface with high-intensity light, a synchronization device 6 such as a rotary encoder disposed at an end of a shaft of the impression cylinder 3 to obtain a synchronizing (registration) signal in the feed direction of the printed paper discharged with the rotation of the printing machine, and a control unit 7 which is inputted with signals from the camera unit 4 and the synchronization device 6. In the control unit 7, reference image data of a correctly printed paper surface taken in by the camera unit 4 at the beginning of the printing operation is compared with image data of a printed paper surface to be checked taken in by the camera unit 4 afterward during the printing operation synchronizing with the signal from the synchronization device 6 to determine whether or not the difference in level between both data is within a predetermined tolerable range, thereby checking the quality of printing. When the control unit 7 determines the presence of a defect print such as an oil stain, the position of the defect is displayed on a CRT display, an alarm is sounded, and a tape inserter 8 or the like is operated to make a marking for identification of the defective print in a subsequent step.

In FIG. 7, numeral 9 indicates an air blow type paper holding device, and numeral 10 indicates a paper discharge cylinder.

During the printing operation, the printing speed may be increased or decreased as needed for stability of the printing density, condition of paper at the paper feed or paper discharge unit, or in view of production control. In such a case, due to the characteristics of the camera unit 4 of the quality inspection device for printed matters, since the amount of light received by the light receiving element is varied, which results in errors in the determination of quality of the printed matters, a correction for speed is made to maintain the level of received light regardless of such variations in printing speed.

As an example of such correction for speed, there has heretofore been proposed a method in which the gain for the image signals from the light receiving element is controlled by an AGC circuit, but this method alone is too narrow in the range of correction compared to the range of variations in printing speed.

SUMMARY OF THE INVENTION

In accordance with the present invention, there is provided a device for correcting for changes in light reflected by the printed matter arising from variations of the feed speed of the printed matter. The device comprises a graduated neutral density filter disposed on an optical axis of a detector, and in front of a light receiving element of the detector. The graduated neutral density filter is adjusted in position relative to the optical axis of the detector in dependence on a signal provided by a feed speed detection means for detecting the feed speed of the printed matter. Means are provided for adjusting the position of the neutral density filter in dependence on the signal provided by the speed detection means to adjust the position of the graduated neutral density filter relative to the optical axis in response to variations in the speed of the printed matter, thereby varying the density of the graduated neutral density filter on the optical axis. As a result, the light receiving element can be provided with a constant level of light without regard to variations in the feed speed of the printed matter.

BRIEF DESCRIPTION OF THE DRAWINGS

FIG. 1 is a schematic view showing speed correction.

FIG. 2 is a schematic view showing the entire structure.

FIG. 3 is a circuit diagram.

FIG. 4 is a processing flow chart by a CPU.

FIG. 5 is a circuit diagram of another embodiment.

FIG. 6 is a schematic view showing position detection means.

DETAILED DESCRIPTION OF PREFERRED EMBODIMENTS

Figure 1:
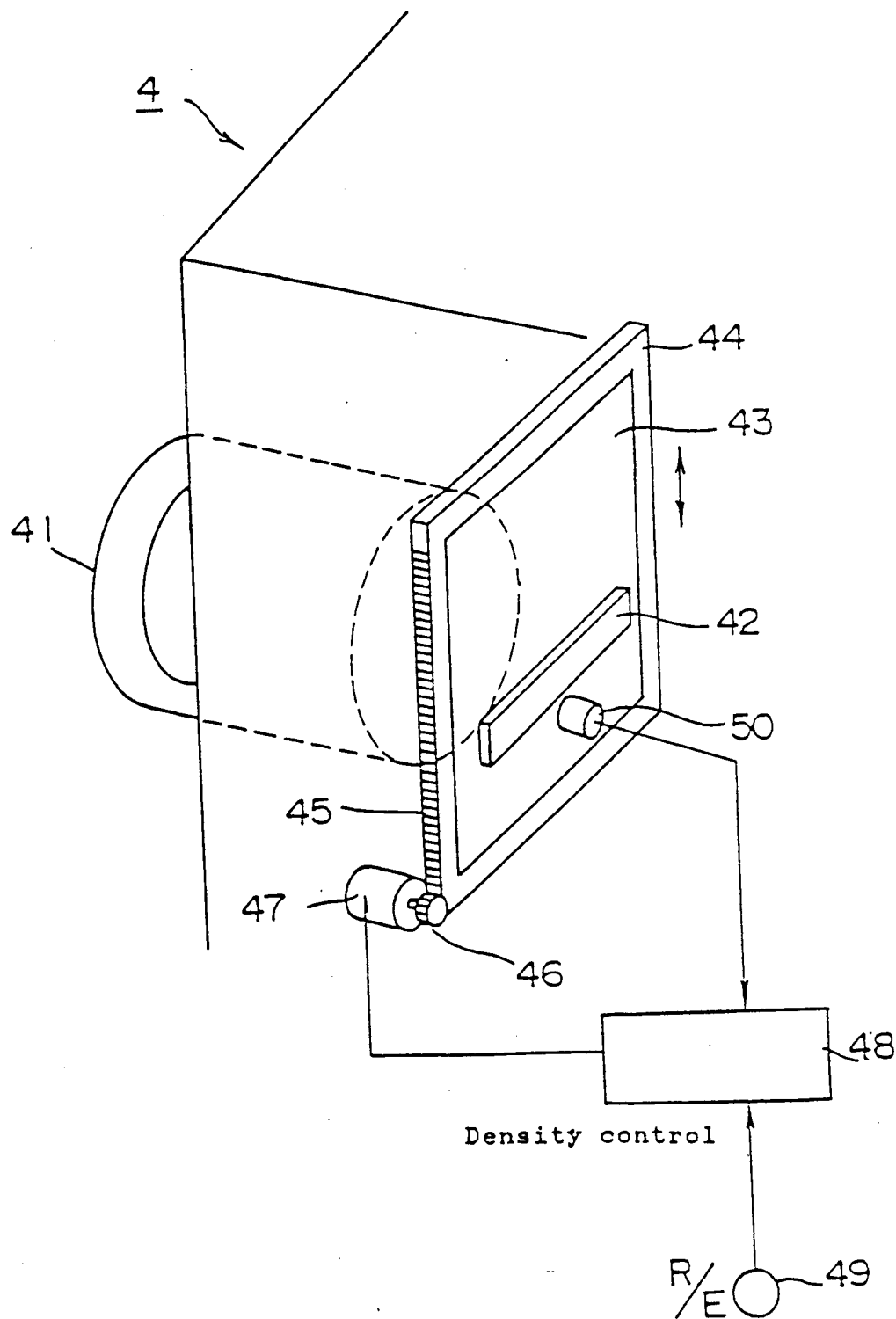
FIG. 1 to FIG. 6 relates to embodiments of the present invention.
Figure 2:
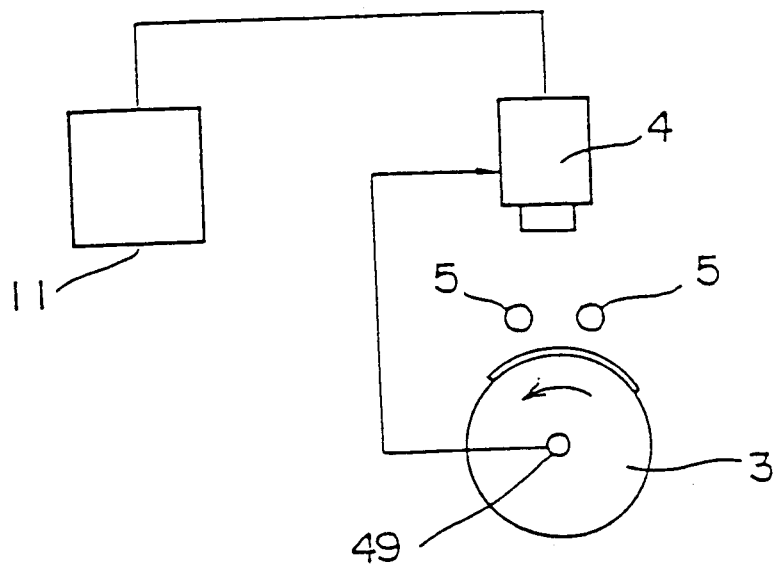

The present invention will now be described in detail with reference to FIG. 1 to FIG. 6. FIG. 1 is a schematic perspective view showing the interior of a camera unit 4. Referring to FIG. 1, a light receiving element 42 such as a CCD is disposed on an optical axis of a camera lens 41 of the camera unit 4. The light receiving element 42 is to output image information in density level for each line of a printed image, which receives reflected light from a printed matter on a cylinder 3 as shown in FIG. 2.

On the optical axis between the camera lens 41 and the light receiving element 42 is disposed a graduated neutral density filter (hereinafter referred to as "ND filter") 43 which is mounted to a supporting plate 44. This ND filter 43 has continuous changes in density (gradation) in the vertical direction, and the same density has almost the same transmittance regardless of the wavelength. A rack 45 is provided at the side of the supporting plate 44 and is connected to a rotary shaft of a drive motor 47 through a pinion 46 engaging with the rack 45. Therefore, by the rotational driving of the drive motor 47, the supporting plate 44 and in turn the ND filter 43 are moved, for example, upward when the drive motor 47 rotates in the forward direction, and downward when the drive motor 47 rotates in the reverse direction.

Operation instruction for the drive motor 47 is outputted from a camera density control circuit 48. The camera density control circuit 48 is connected with a synchronization device 49 for detecting the feed speed such as a rotary encoder attached to the cylinder 3 to detect its rotation, from which a feed speed signal is taken in.

The camera density control circuit 48 is also connected to a density sensor 50 disposed in the vicinity of the light receiving element 42. The density sensor 50 is to detect the density of a light receiving part of the ND filter 43 of the light receiving element 42, that is, to detect the intensity of light passed through the ND filter 43 in the vicinity of the light receiving element 42.

FIG. 2 shows the cylinder 3, a lighting unit 5, and a determination processing circuit 11, centering on the camera unit 4. Of these, the lighting unit 5 disposed between the camera unit 4 and the cylinder 3 comprises a high illuminance lamp such as a high-intensity fluorescent lamp or a xenon lamp.

In the camera unit 4, the light receiving element 42 shown in FIG. 1 is connected to the determination processing circuit 11 shown in FIG. 2 and, in the determination processing circuit 11, for image data received by the camera unit 4, a reference data is compared with a determination data to determine the quality of the determination data, thereby achieving the function of the quality inspection device.

The circuit configuration of the camera density control circuit 48, the drive motor 47, the density sensor 50, and the synchronization device 49 will be described with reference to FIG. 3. The synchronization device 49 is connected to a rotational speed detection circuit 481 in the camera density control circuit 48, and the detection circuit 481 reads rotational speed based on the output of the synchronization device 49. The rotational speed detection circuit 481 is connected to a data bus 482 and to a CPU 483 and a D/A converter 484 through the data bus 482. Therefore, by an instruction of the CPU 483, speed from the synchronization device 49 is read by the rotational speed detection circuit 481, and the speed is converted to a density value for the control of the position of adjustment of the graduated neutral density filter 43. The processing flow is shown in FIG. 4.

The D/A converter 484 is connected to a comparator 485. The comparator 485 compares output of the D/A converter as a density value corresponding to the speed with an actual density value of the density sensor 50 and outputs the difference. The comparator 485 is connected to a motor driver, and the motor driver 471 drives the drive motor 47 until the output of the comparator 485 is zero (no difference). The drive motor 47 and the motor driver 471 are speed feedback controlled.

Thus, the density of the ND filter corresponding to the speed is feedback controlled, and a constant light receiving amount is obtained at the light receiving element independently of the speed.

Figure 3:
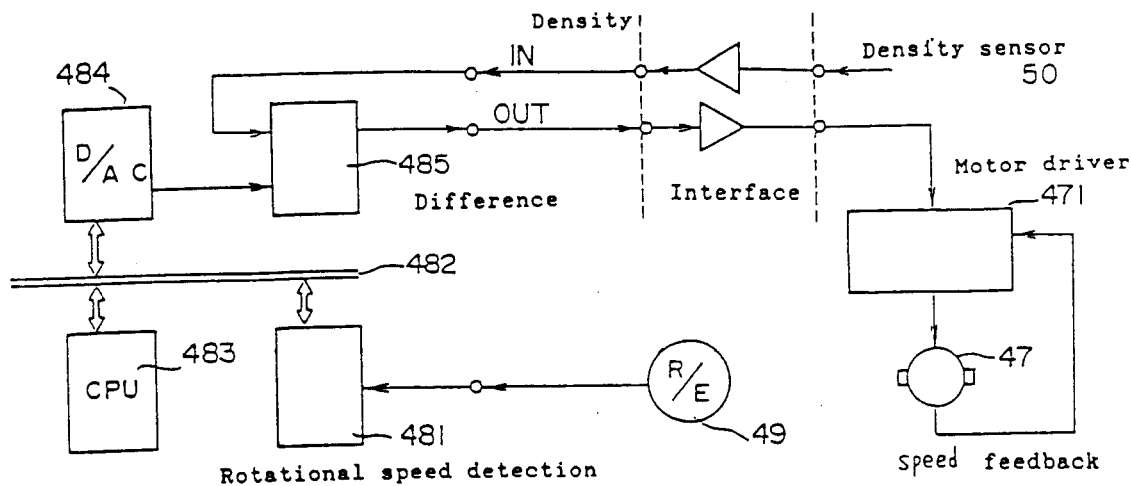
Figure 4:
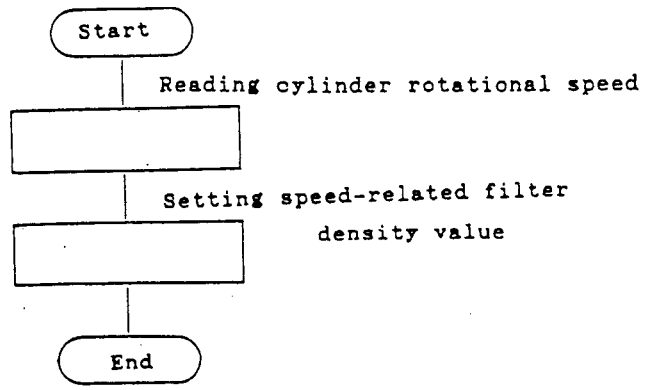

The examples shown in FIG. 1 and FIG. 3 use the density sensor 50 to make feedback control and require conversion between the rotational speed and density. However, when exact matching is possible between the density value corresponding to the ND filter 43 and its position, that is, the rotational position of the drive motor 49, an optimal density of the ND filter 43 is obtained by merely controlling the rotational position of the drive motor 47, without the need for the density sensor.

Figure 5:
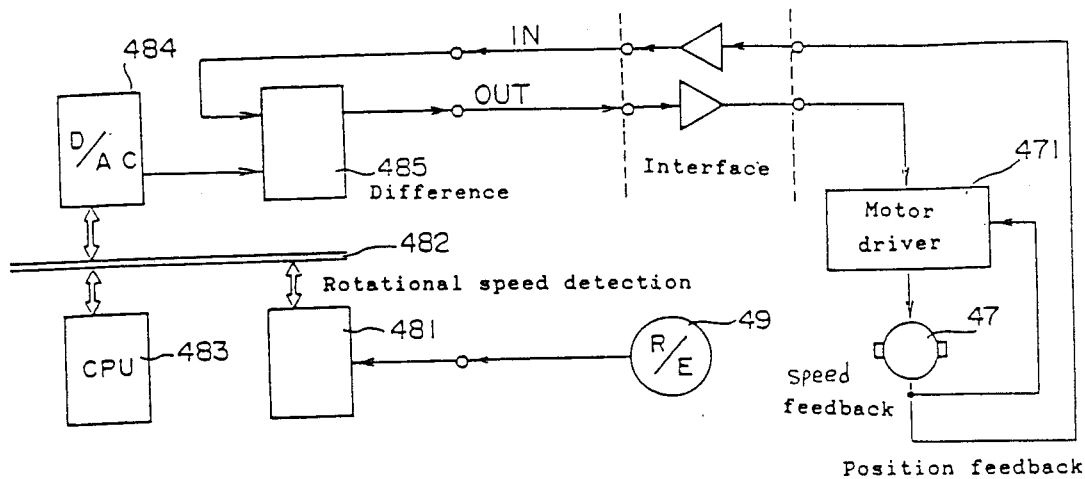

FIG. 5 shows an example of circuit which makes positional control of the drive motor 47 without using the density sensor. Referring to FIG. 5, by an instruction of the CPU 483, speed read by the rotational speed detection circuit 481 from the synchronization device 49 is converted to a position corresponding to the density value of the ND filter 43 according to a speed-position conversion table written in a ROM of the CPU 483, and then analog converted by the D/A converter 484. The comparator 485 compares the position signal of the D/A converter 484 with a position feedback signal of the drive motor 47, and the motor driver 471 is driven so that the difference in position is zero, thus controlling the drive motor 47. Thus, the feedback control system does not use density as a parameter but uses rotational position of the drive motor 47 as a parameter.

Figure 6:
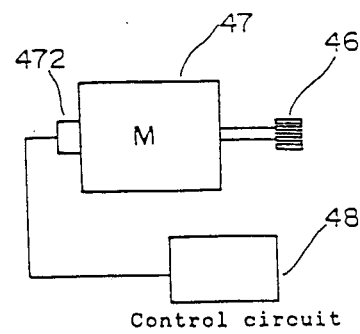
Figure 7:
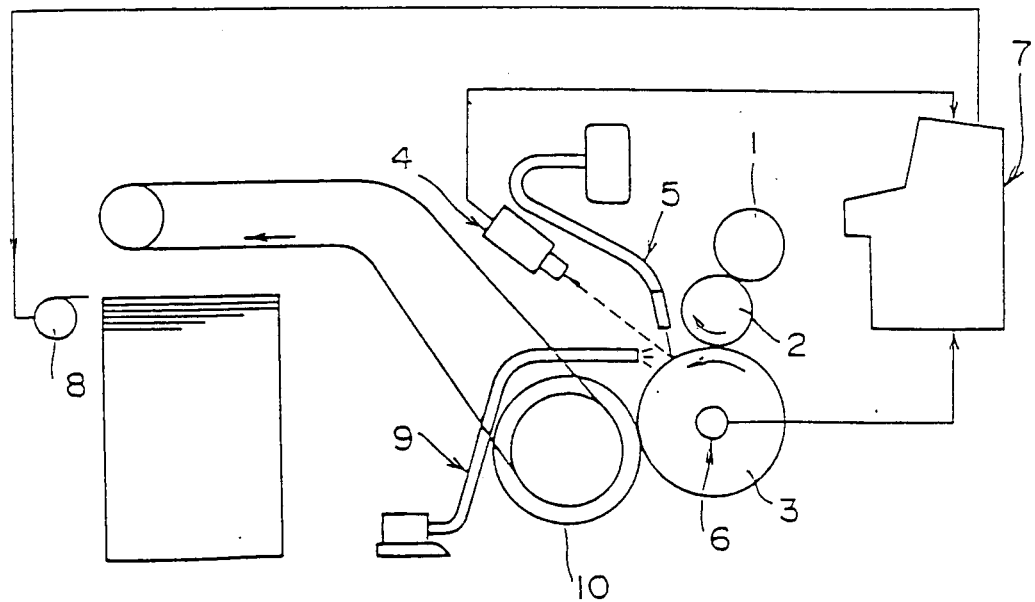
FIG. 7 is a schematic view showing structure of a prior art quality inspection device for printed matter.

FIG. 6 shows an example which uses means for detecting motor rotational position and rotational speed to make position feedback of the drive motor 47, which has a rotary encoder 472 mounted to the rotary shaft of the motor 47. Alternatively, a potentiometer as rotational position detection means and a tachogenerator as rotational speed detection means may be attached to the rotary shaft of the drive motor 7.

As described above, with the present invention, light receiving amount is controlled to a constant value even at a rise or changes in speed of the feed unit for the printed matter, thereby obtaining a constant output and providing stable inspection despite speed variations. This enables a 100% sampling inspection.

We claim:

1. A quality inspection device for printed matter, comprising:
    a camera unit including a graduated neutral density filter disposed on an optical axis of a detector and in front of a light receiving element:
    means for moving said graduated neutral density filter relative to said optical axis to vary the density of said graduated neutral density filter on said optical axis;
    feed speed detection means for detecting the feed speed of the printed matter; and,
    means for converting the speed detected by said feed speed detection means into a signal operative to adjust the position of said graduated neutral density filter, and thus the density of said graduated neutral density filter on said optical axis in relationship with the feed speed of said printed matter.

2. The quality inspection device of claim 1, in which said light receiving element provides an output signal representative of density-level image information of said printed matter.

3. The quality inspection device of claim 1, in which said means for moving said graduated neutral density filter relative to said light receiving element includes means for converting rotational movement into a linear movement employing a drive motor, a pinion, and a rack.

4. The quality inspection device of claim 1, in which the rotational speed of an impression cylinder is detected by a rotary encoder.

5. The quality inspection device of claim 1, further including a high-intensity light source disposed between the camera unit and an impression cylinder, and operative to provide light reflected from said printed matter.

6. A method for inspecting the quality of printed matter, comprising the steps of:
    detecting the feed speed of said printed matter;

converting the detected feed speed into a signal representative of said feed speed; and,
adjusting the position of a graduated neutral density filter relative to an optical axis of a detector, in order to compensate for variations in light reflected from said printed matter along said optical axis upon variations in said feed speed.

* * * * *